(12) United States Patent
Reinhard et al.

(10) Patent No.: US 9,013,689 B2
(45) Date of Patent: Apr. 21, 2015

(54) ENGINEERED SERS SUBSTRATES EMPLOYING NANOPARTICLE CLUSTER ARRAYS WITH MULTISCALE SIGNAL ENHANCEMENT

(75) Inventors: Bjoern Markus Reinhard, Boston, MA (US); Luca Dal Negro, Cambridge, MA (US)

(73) Assignee: Trustees of Boston University, Boston, MA (US)

( * ) Notice: Subject to any disclaimer, the term of this patent is extended or adjusted under 35 U.S.C. 154(b) by 770 days.

(21) Appl. No.: 13/142,939

(22) PCT Filed: Jan. 11, 2010

(86) PCT No.: PCT/US2010/020640
§ 371 (c)(1),
(2), (4) Date: Jun. 30, 2011

(87) PCT Pub. No.: WO2010/081088
PCT Pub. Date: Jul. 15, 2010

(65) Prior Publication Data
US 2011/0267614 A1 Nov. 3, 2011

Related U.S. Application Data

(60) Provisional application No. 61/143,670, filed on Jan. 9, 2009.

(51) Int. Cl.
*G01J 3/44* (2006.01)
*G01N 21/65* (2006.01)
*B82Y 30/00* (2011.01)

(52) U.S. Cl.
CPC .............. *G01N 21/658* (2013.01); *B82Y 30/00* (2013.01)

(58) Field of Classification Search
CPC .................................................... G01N 21/658
USPC .......................................................... 356/301
See application file for complete search history.

(56) References Cited

U.S. PATENT DOCUMENTS 6,699,724 B1 * 3/2004 West et al. .................... 436/525
7,151,598 B2 12/2006 Poponin
(Continued)

OTHER PUBLICATIONS

Liu et al. "Planned Nanostructures of Colloidal Gold via Self-Assembly on Hierarchically Assembled Organic Bilayer Template Patterns with In-situ Generated Terminal Amino Functionality", 2004, Nano Letters, vol. 4, No. 5, pp. 845-851.*
(Continued)

*Primary Examiner* — Kara E Geisel
(74) *Attorney, Agent, or Firm* — BainwoodHuang

(57) ABSTRACT

Defined nanoparticle cluster arrays (NCAs) with total lateral dimensions of up to 25.4 μm by 25.4 μm have been fabricated on top of a 10 nm thin gold film using template guided self-assembly. This approach provides precise control of the structural parameters in the arrays allowing a systematic variation of the average number of nanoparticles in the clusters (n) and the edge to edge separation (Λ) between 1<n<20 and 50 nm≤Λ≤1000 nm, respectively. Investigations of the Rayleigh scattering spectra and surface enhanced Raman scattering (SERS) signal intensities as a function of n and Λ reveal direct near-field coupling between the particles within individual clusters, whose strength increases with the cluster size (n) until it saturates at around n=4. Our analysis shows that strong near-field interactions between individual clusters significantly affects the SERS signal enhancement for edge-to-edge separations Λ<200 nm. The observed dependencies of the Raman signals on n and Λ indicate that NCAs support a multiscale signal enhancement which originates from simultaneous inter- and intra-cluster coupling and |E|-field enhancement. The NCAs provide strong SERS signals of bacterial cells thus enabling a rapid and reliable spectral identification of bacteria.

10 Claims, 10 Drawing Sheets

(56) References Cited

U.S. PATENT DOCUMENTS

| | | | |
|---|---|---|---|
| 2003/0059820 A1* | 3/2003 | Vo-Dinh | 356/301 |
| 2004/0180379 A1* | 9/2004 | Van Duyne et al. | 435/7.1 |
| 2004/0218184 A1* | 11/2004 | Jorgenson et al. | 356/419 |
| 2004/0241896 A1* | 12/2004 | Zhou et al. | 438/48 |
| 2005/0079551 A1* | 4/2005 | Mizuno et al. | 435/7.1 |
| 2005/0214661 A1* | 9/2005 | Stasiak et al. | 430/22 |
| 2006/0055922 A1* | 3/2006 | Li et al. | 356/301 |
| 2006/0209300 A1* | 9/2006 | Kamins et al. | 356/301 |

OTHER PUBLICATIONS

Stadler et al., "Nanopatterning of gold colloids for label-free biosensing", 2007, Nanotechnology, 18, pp. 1-4.*

Brown, R.J.C., et al., "Nanostructures and nanostructured substrates for surface-enhanced Raman scattering (SERS)," Journal of Raman Spectroscopy, vol. 39, p. 1313-1320, published on-line Jun. 11, 2008.

Dallapiccola, R., et al., "Quasi-periodic distribution of plasmon modes in two-dimensional Fibonacci arrays of metal nanoparticles," Optics Express Journal, vol. 16, No. 8, published on-line Apr. 4, 2008.

Gopinath, A., et al., "Photonic-Plasmonic Scattering Resonances in Deterministic Aperiodic Structures," Nano Letters vol. 8, No. 8, p. 2423-2431, published on-line Jul. 23, 2008.

Xia, Y., et al., "Template-Assisted Self-Assembly of Spherical Colloids into Complex and Controllable Structures," Advanced Functional Materials Journal, vol. 13, No. 12, p. 907-918, Dec. 2003.

* cited by examiner

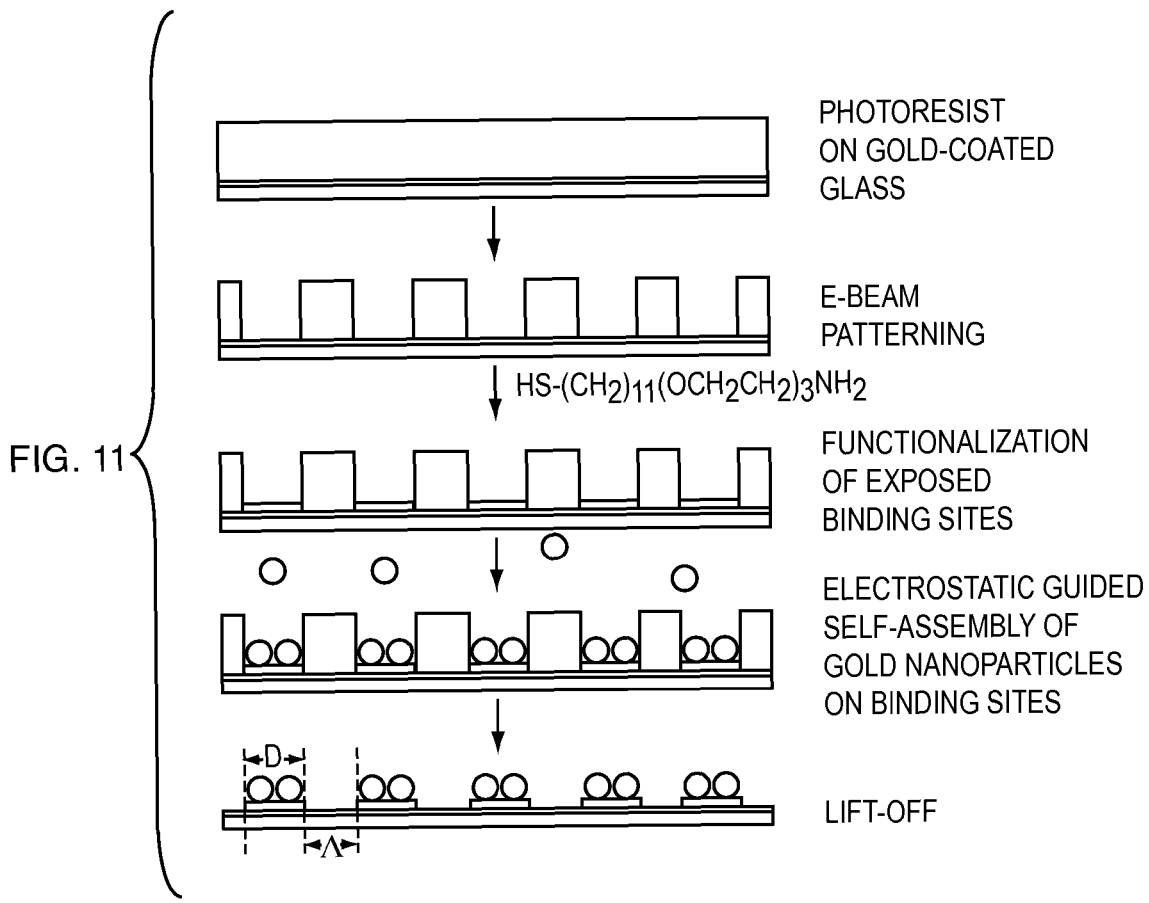
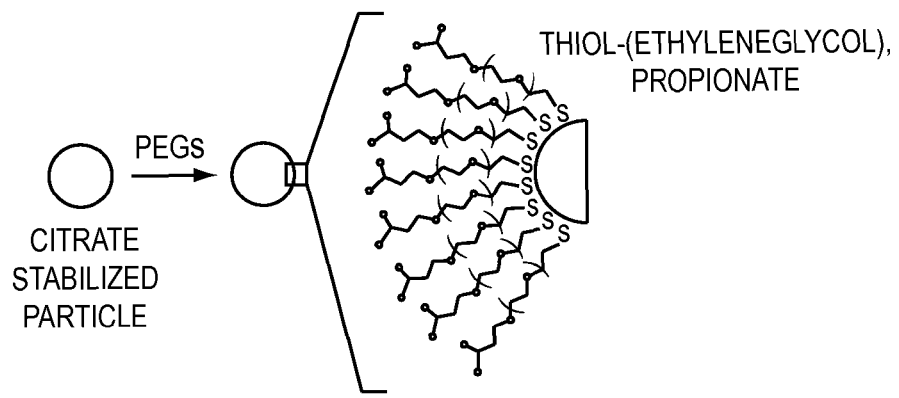
FIG. 12

ENGINEERED SERS SUBSTRATES EMPLOYING NANOPARTICLE CLUSTER ARRAYS WITH MULTISCALE SIGNAL ENHANCEMENT

STATEMENT OF FEDERAL RIGHTS

The invention was made with Government support under Contract No. W911NF-06-2-0040 awarded by the Army Research Office. The Government has certain rights in the invention.

BACKGROUND

The intensities and frequencies of vibrational transitions measured in Raman spectra provide unique chemical signatures of molecular species, but the sensitivity of Raman spectroscopy suffers from the relatively low cross-section of inelastically scattered Raman photons. It has been demonstrated that the magnitude of Raman cross-sections can be greatly enhanced when the Raman-active molecules are placed on or near a roughened noble metal surface. Since then a wide variety of substrates have been found to enable surface enhanced Raman spectroscopy (SERS) such as aggregated noble metal colloids, metal island films, metal film over nanospheres, particles grafted on silanized glasses, regular holes in thin noble metal films and regular nanoparticle arrays.

In general, traditional SERS substrates can be divided into two fundamental substrate classes: random and engineered substrates. Random substrates like fractal nanoparticle agglomerates can support localized dipole modes which lead to high SERS signal enhancements. However, the resonance wavelength, the precise locations of the spots of giant $|E|$-field enhancement—so called hot-spots—and the reproducibility of their enhancement factors are difficult to control in completely random structures. Another disadvantage specific to fractal nanoparticle aggregates is that their mass density, and therefore the hot-spot density, decreases with increasing fractal size.

Challenging applications of SERS in single molecule spectroscopy or whole organism fingerprinting would greatly benefit from engineered SERS substrates with rational design criteria that generate high SERS enhancement reproducibly at spatially defined locations. Consequently, regular nanoparticle arrays and other nanofabricated SERS substrates, whose characteristic structural parameters can be accurately controlled, are attracting interest as SERS substrates with reproducible, high enhancement factors "by design". The SERS enhancement in noble metal nanoparticle arrays depends on both the properties of the constitutive building blocks (nanoparticles) as well as the characteristics of their arrangement. In general two separate electromagnetic regimes govern the collective response of periodic metal-nanoparticle arrays: near and far-field coupling. When the particles are separated by short distances up to approximately $D=1/k_0=\lambda_0/2\pi$ (with $k_0$ and $\lambda_0$ being the free space wavenumber and wavelength, respectively), strong quasi-static near-field interactions dominate the response of the array. Consequently, localized modes with strongly enhanced local fields are excited. When the particles are separated by larger distances, far-field diffractive coupling between the particles becomes dominant.

In the near-field coupling regime the field enhancement and corresponding SERS intensity arising from periodic arrays of nanoparticles sharply increases with decreasing inter-particle separation. Both theoretical and experimental studies have shown that regions of high $|E|$-field enhancement are located in the junction between individual particles. The $|E|$-field enhancement in these spatially confined hot spots can be orders of magnitude larger than on the surface of individual particles. Due to the rapid decay of the field strength with inter-particle separation and the $|E|^4$ scaling of the SERS signal, very short inter-particle separations are vital in order to maximize the Raman enhancement in the near-field coupling regime. Ideally, the analyte molecules are placed in the junctions between nearly touching metal surfaces.

SUMMARY

It remains challenging to create junction plasmons at predefined locations and with nanometer accuracy in current top-down fabrication methods such as electron beam (e-beam) lithography. The spatial resolution of e-beam lithography is limited by laterally scattered secondary electrons, which makes it difficult to reproducibly fabricate arrays with inter-particle separations of less than 10 nm. In order to overcome this limitation, an alternative approach is demonstrated here that can be used to engineer SERS substrates with nanoscale inter-particle separations reliably. Template guided chemical self-assembly is used to create nanoparticle cluster arrays (NCAs) of defined size with nanoscale inter-particle separations at predefined pattern locations. E-beam lithography is not used to directly generate plasmonic structures but instead to define binding sites on which chemically synthesized gold nanoparticles can assemble. Consequently, "hot" inter-nanoparticle junctions at predefined locations in a regular array can be created, enabling the possibility to control and optimize both near- and far-field noble metal nanoparticle interactions.

The description herein includes a systematic characterization of the optical scattering spectra and the Raman signal intensity enhancements of these NCAs as function of cluster size n and cluster edge-to-edge separation Λ, comparing their performance with non-patterned colloidal gold films and periodic two-dimensional nanodisc arrays, and an application for spectral identification of bacterial pathogens. Rapid bacteria diagnostics are vital for improving the treatment outcomes of serious infections and ensuring the appropriate use of antibiotic strategies. A SERS based approach for bacterial detection and identification relies on signal amplification techniques (PCR), and thus offers several potential advantages, such as speed, reduced susceptibility to contamination problems, ease-of-use and mixture resolution for rapid, specific and sensitive bacterial diagnostics. The key requirement for the success of this methodology is the production of SERS substrates with large and reproducible signal enhancement. In this study, we demonstrate that NCAs provide reproducible SERS signals from different bacteria species including *Escherichia coli*, *Bacillus cereus*, and *Staphylococcus aureus*.

Overview of Methods

Nanofabrication of Particle Binding Sites.

A fabrication process is described which begins with spin-coating 180 nm polymethyl methacrylate (PMMA) 950 photoresist on top of Au-coated (10 nm Au film) glass slides. The substrates are subsequently soft-baked at 180° C. for 20 min. Periodic patterns of nanowells are then written with a Zeiss SUPRA 40VP SEM equipped with Raith beam blanker and a nanopattern generation system (NPGS). After e-beam writing, the photoresist is developed in methyl isobutyl ketone (MIBK). Periodic patterns of nanowells with inter-well separations (edge to edge) of 50 nm, 100 nm, 150 nm, 200 nm, 400 nm, 600 nm, 800 nm, and 1000 nm are generated by this procedure.

Template Guided Self-Assembly of Gold Nanoparticle Clusters.

Commercial citrate-stabilized 40 nm Au particles in aqueous solution are concentrated by a factor of 10 by centrifugation. 100 μL of the concentrated gold sol is then incubated with 5 μL of a 10 mM thiol-$EG_7$-propionat (EG=ethylene glycol) aqueous solution overnight at room temperature. The particles are cleaned by centrifugation and re-suspended in a 10 mM phosphate buffer pH=8.6 containing 40 mM NaCl. The patterned gold substrates are incubated with a 1 mM aqueous solution of thiol-$(CH_2)_{11}EG_7$-Amine for 15 minutes and then washed with water. The Au particles solution is added on the top surface of the substrates and incubated for 1 h. The particle solution is removed by washing with water. After the samples are dried, PMMA liftoff is performed with 1-Methyl-2-pyrroldinone.

Dark-Field Scattering Characterization of Periodic Cluster Arrays.

Scattering images of the particle cluster arrays were recorded using an upright microscope (Olympus BX51 WI). The nanoparticle arrays were immersed in index-matching oil ($n_r$=1.5) and illuminated with unpolarized white-light from a 100 W tungsten halogen lamp using an oil dark-field condenser (NA 1.2-1.4) in transmission mode. The light scattered from the arrays was collected with a 60× oil immersion objective (NA=0.65) and imaged using a digital camera with an active area of 620×580 pixels. The microscope was also equipped with a 150 mm focal length imaging spectrometer (Acton Research, InSpectrum 150) and a back-illuminated CCD detector (Hamamatsu INS-122B) that enabled the spectral analysis of the scattered light using a 150 lines/mm grating. The scattering spectra were background corrected by subtraction of the scattering signal from an equal-size, non-patterned adjacent area. The scattering spectra were additionally corrected by the excitation profile of the white light source by normalizing with the scattering spectrum of an ideal white light scatterer on top of the gold film.

SERS Measurements.

A Renishaw Raman microscope (model RM-2000) capable of ~22λ spatial resolution was used to observe the scattering excited by a 785 nm diode laser. The frequency calibration was set by reference to the 520 cm-1 silicon phonon mode. Paramercaptoaniline (pMA) was used to characterize the field enhancement on the cluster arrays. The saturated aqueous pMA solution was kept on the substrate for 10 min before removing with a flow of nitrogen gas. A 50× objective (numerical aperture NA=0.78) was used for signal collection. SERS spectra were acquired with incident laser powers in the 0.44 to 7.34 mW range and acquisition times of 10-60 seconds.

Calculation of Approximate SERS Enhancement Factors for Paramercaptoaniline (pMA).

SERS enhancement factors, G, were calculated following standard procedures G is defined here by: G=(ISubstrate/NSubstrate)*(NReference/IReference) where ISubstrate is the Raman intensity of a monolayer of pMA on the SERS substrate and IReference is the Raman signal due to a pMA crystal. NReference and NSubstrate refer to the number of pMA molecules in a monolayer on the SERS substrate and in the focal region of the crystal, respectively. An aperture was used to confine the sample detection area to σ=2.5 μm×25 μm. NSubstrate was obtained as the ratio of active nanoparticle cluster array area within the detection area and the cross-section of the pMA molecule ($\pi_{pMA}$=0.3 $nm^2$). For NCAs the active area is estimated by multiplying the number of clusters in the laser spot with the product of the average number of particles in the clusters and the surface area of one hemisphere of a 40 nm gold nanoparticle. NReference was calculated assuming a confocal depth of 14 μm and a density of 1.06 g/mL for solid pMA (molecular weight=125 g/mol). For non-patterned colloidal gold films the surface-densities of 40 nm gold particles were obtained by counting the number of particles in representative SEM images with defined dimensions. Then NSubstrate was calculated using the same assumptions as in the case of the NCAs. In the case of smooth nanodisc arrays, NSubstrate was determined as the ratio of active area (number of discs in the detection area multiplied by the exposed disc surface area) and $\sigma_{pMA}$.

Bacteria Growth and Sample Preparation.

Gram-negative bacteria *Escherichia coli* (ATCC #12435), and Gram-positive bacteria *Bacillus cereus* (ATCC #14579) and *Staphylococcus aureus* (ATCC #25904) were grown in 15-20 mL of LB (Sigma) for ~5 h at 37° C. until they reached an OD600=~0.6. About 4 mL of each culture solution was washed, centrifuged and vortexed four times with Millipore water. Finally, the pellet was suspended in 0.25 mL of water. About 1 μL of the bacteria suspension was placed on the cluster arrays, and after the water had evaporated (~2 minutes), the samples were transferred into the Raman microscope to record SERS spectra.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 11 is a set of diagrams illustrating a method and corresponding workpieces in fabricating a SERS substrate;

FIG. 12 is a diagram depicting binding of a gold nanoparticle to a binding site;

DETAILED DESCRIPTION

Figure 1:
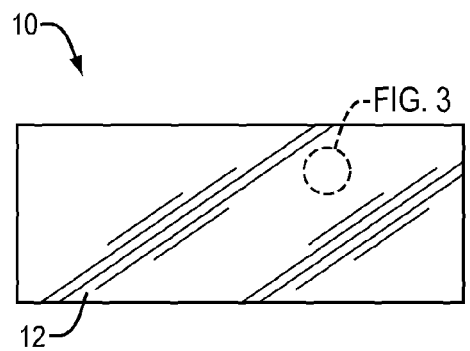
FIGS. 1 and 2 are a top view and side view respectively of a substrate for use in SERS spectroscopy.
Figure 2:
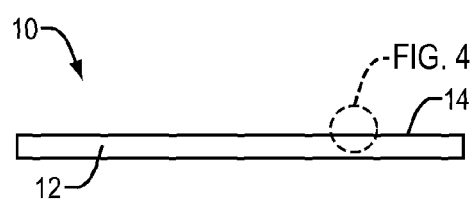
Figure 3:
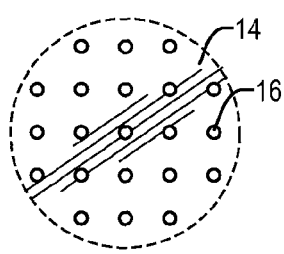
FIGS. 3 and 4 are magnified top and side views respectively of the substrate of FIGS. 1 and 2.
Figure 4:
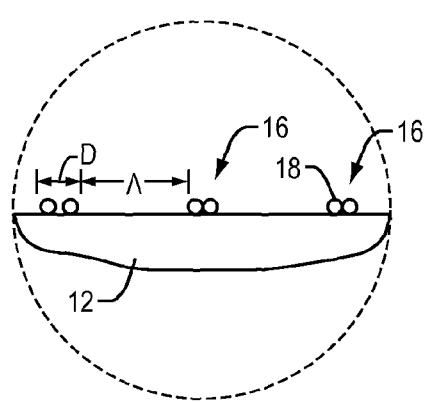

FIGS. 1 and 2 show top and side views respectively of a substrate 10 for use in SERS spectroscopy in the form of a glass slide 12 having a patterned top surface 14 used as the active SERS surface. FIG. 3 illustrates a close-up view of the top surface 14, on which is formed an array of clusters 16 of gold nanoparticles. FIG. 4 shows a set of adjacent clusters 16 in side view. The schematic side view of FIG. 4 shows nanoparticles 18 of each cluster 16. FIG. 4 also shows dimensions D and Λ, with D being the diameter of the binding sites at which each cluster 16 is located and Λ being an edge-to-edge separation of the clusters 16. The term "cluster size" is used herein to refer to the number of nanoparticles 18 per cluster 16. It will be appreciated that the cluster size is a function of both the dimension D and the diameter of a nanoparticle 18.

Figure 5:
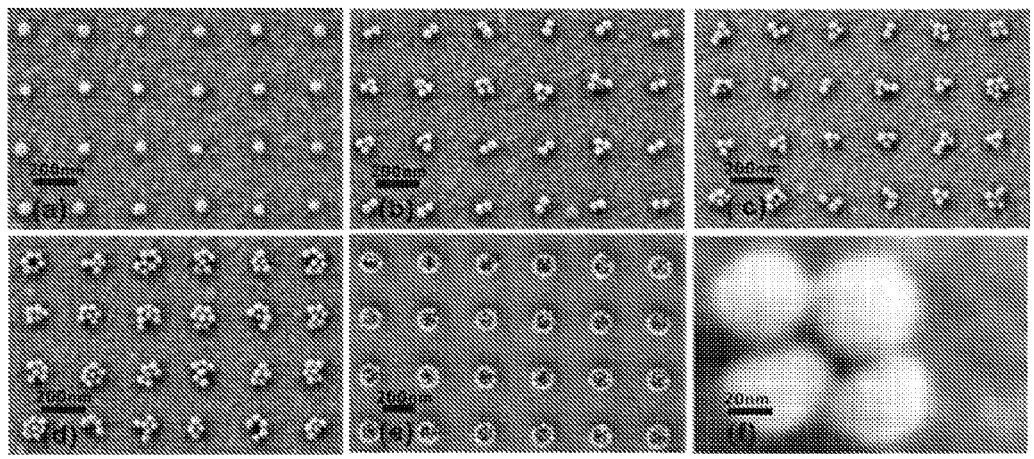
FIGS. 5 and 6 are sets of scanning electron microscope (SEM) images of a top surface of a SERS substrate.

FIG. 5 shows scanning electron microscope (SEM) images of sections of the fabricated cluster arrays 16 with a fixed edge-to-edge separation (Λ=200 nm) but varying binding site diameters (D=50 nm, 80 nm, 100 nm, 130 nm, 200 nm). The SEM images show regular arrays of two-dimensional nanoparticle clusters with varying cluster size. The images confirm that template guided self-assembly approach (described below) leads to a spatially confined particle clustering into discrete assemblies. FIG. 5 also shows that the average cluster size (i.e. number of particles in the clusters) can be conveniently controlled by varying the binding site diameter D. For D=50, regular arrays of individual 40 nm gold nanoparticles with a high degree of translational symmetry are found. With increasing D, larger clusters are formed that exhibit some geometry and size variability. Even under ideal assembly conditions a distribution of particle numbers and cluster geometry results from the natural size dispersion of the colloid used (coefficient of variation <20%). The low number of particles in the clusters makes the variation in the cluster size and shape most striking for intermediate binding sizes of D=80 nm to 130 nm. In contrast, the larger clusters appear more homogenous again.

Image (f) of FIG. 5 shows a particle cluster in the D=80 nm NCA at higher magnification. As evident the particle clusters contain holes, junctions, and crevices between a few nanometer-spaced gold nanoparticles. These nanoparticle-gap structures are known to support a strong |E|-field localization which can induce a strong enhancement of the dipole moment of the analyte molecules. The enhanced molecular dipole moments and the amplification of the re-radiated Raman scattered light through the noble metal nanostructures lead to a strong enhancement of the SERS signal.

Figure 6:
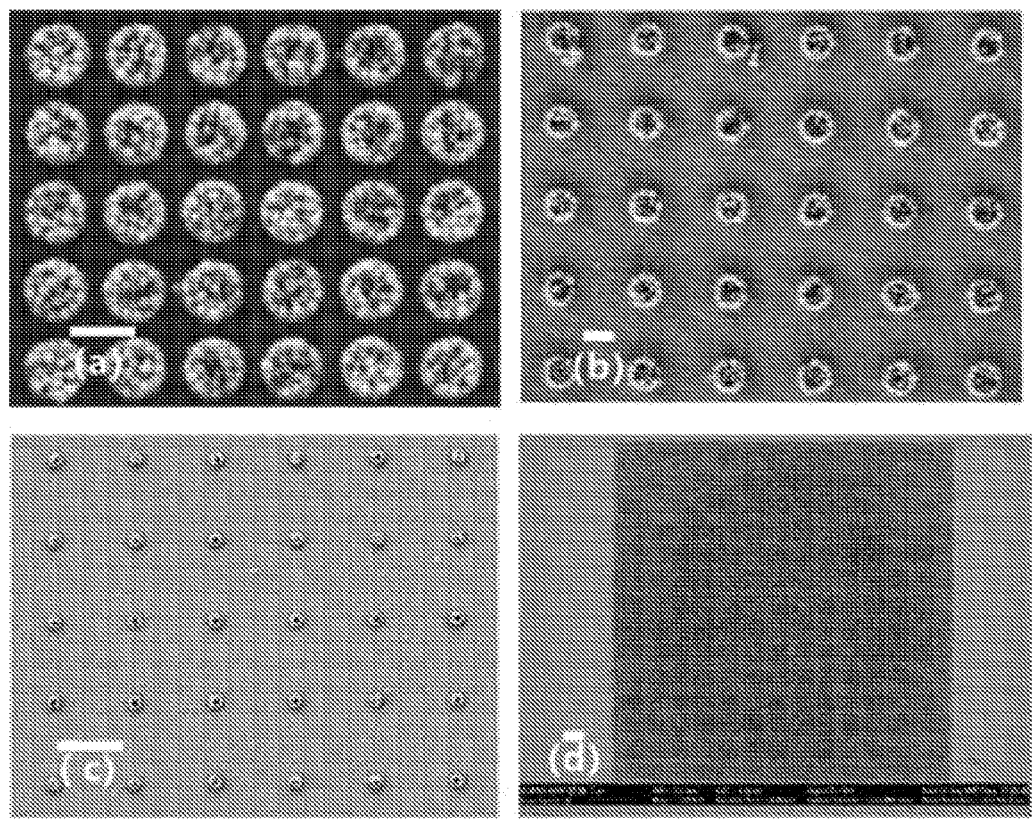

To test the field enhancing effect of inter-cluster coupling, NCAs were made with varying cluster edge-to edge separation Λ. NCAs with Λ=50, 100, 150, 200, 400, 600, 800, and 1000 nm and fixed binding site diameters between D=50-200 nm were made. Of these, FIG. 6 shows examples with fixed binding site diameter D of 200 nm and separations Λ of 50 nm, 200 nm, and 1000 nm. It may be difficult to decrease the edge-to-edge separation significantly below Λ=50 nm, especially for larger cluster sizes, because at very short inter-particle separations individual nanoparticles clusters tend to fuse and form continuous lines of nanoparticle clusters across the pattern. Thus, the current template assisted self-assembly approach can generate extended NCAs with a wide range of inter-cluster separation Λ and cluster sizes D, albeit with some potential limitation for the minimum inter-cluster separation. The following description presents a systematically analysis of the optical response and the SERS enhancement as functions of Λ and D to elucidate an understanding the fundamental mechanisms governing the multi-length scale electrodynamic interactions in NCAs.

Influence of the Cluster Edge-to-Edge Separation Λ on the Rayleigh Scattering Spectra of Nanocluster Particle Arrays.

The optical response of dielectrically coated gold nanoparticles on a gold film is determined by the local plasmons of the particles, their interactions through space (near-field and far-field coupling) and by their coupling to delocalized plasmon modes supported by the gold film. The localized modes in the particles can couple with image modes in the gold film as well as with plasmon modes in neighboring particles. In addition, a gold surface which is periodically corrugated by gold nanoparticle clusters can act as a grating coupler. In this case photons incident on this surface can efficiently excite a propagating surface plasmon in the gold film, which can be Bragg-scattered from the regular cluster arrays.

Given these different electromagnetic interactions between localized and delocalized plasmon modes in NCAs, it is challenging to quantitatively predict the optical response of the nanoparticle cluster arrays. As a first step towards an understanding of these potential SERS substrates the spectral response of the NCAs can be characterized as a function of the controllable template parameters Λ and D. To that end arrays may be fabricated with varying cluster edge-to-edge separations Λ=50-1000 nm but constant cluster binding sizes D=200 nm. Since we kept the total number of binding sites constant for all inter-cluster separations D, the total area of the fabricated arrays varies from 25.4 μm×25.4 μm for Λ≤1000 nm to 16 μm×16 μm for Λ=50 nm. Due to the small size of the arrays a spectral characterization of the arrays using extinction spectroscopy would be challenging. Instead, we decided to characterize the optical response of the NCAs using Rayleigh scattering spectroscopy, which can be conveniently performed in a darkfield microscope. With the help of a darkfield condenser the excitation light can be injected into the specimen plane at such a steep angle from the bottom that only scattered light can reach the objective on top of the sample. The geometrical constraints of the darkfield illumination allows effective discrimination of the excitation light, and is therefore an ideal technique for probing the plasmon resonances of nanostructures which do not provide a strong extinction. Rayleigh scattering spectroscopy is routinely used to investigate the optical properties of a wide range of nanostructured plasmonic materials, ranging from single noble metal nanoparticles over regular one- and two-dimensional arrays of gold nanoparticles to deterministic aperiodic arrays of gold nanoparticles.

Figure 7:
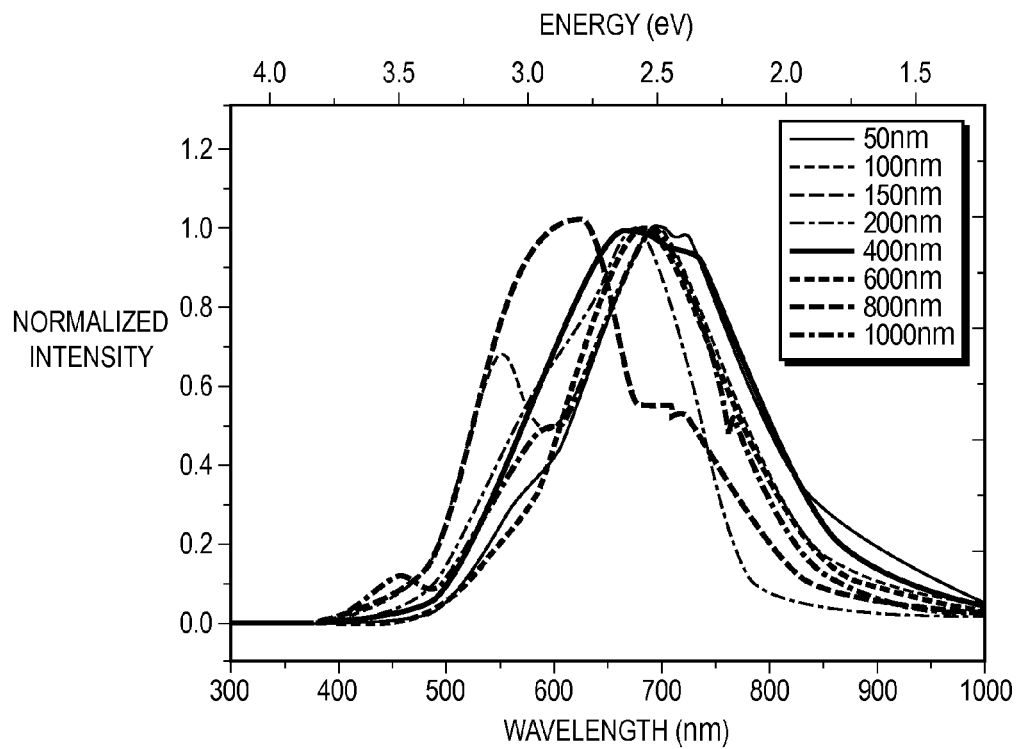
FIG. 7 is a plot of normalized SERS scattering spectra for various values of inter-cluster separation.
Figure 8:
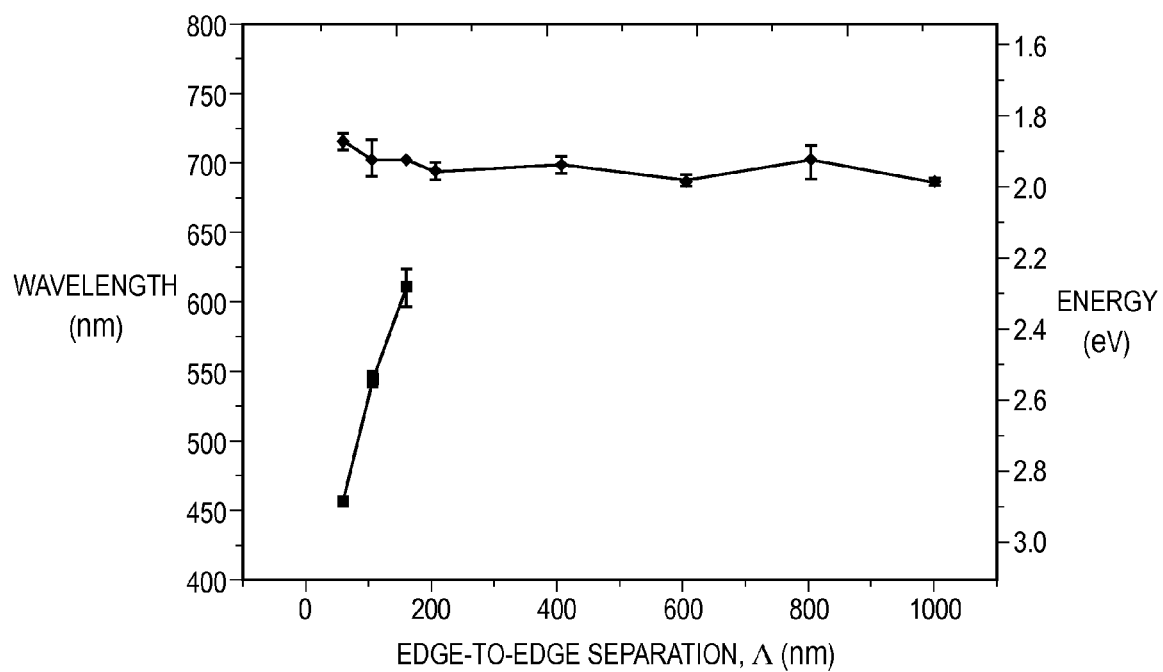
FIG. 8 is a plot of peak resonance wavelength as a function of inter-cluster separation.

FIG. 7 shows the normalized scattering spectra of the fabricated NCAs with varying Λ but fixed D=200 nm. The displayed spectral intensities were not corrected by the different filling fractions of the arrays, since we focus on the spectral shifts originating from differences in the array parameters in this study. All of the spectra in FIG. 7 show a broad peak around 700 nm, which we assign to the nanoparticle cluster resonance coupled via propagating surface plasmons in the gold support as has been described elsewhere. In addition to this coupled nanoparticle cluster resonance, NCAs with Λ<200 nm exhibit a separate short wavelength band which strongly red-shifts with increasing Λ. In FIG. 8, the peak resonance wavelengths of these two bands, determined by Gaussian best fits, are plotted as a function of Λ. The maximum of the short wavelength band shifts from ~455 nm (Λ=50 nm) over ~545 nm (Λ=100 nm) to ~613 nm (Λ=150 nm). For Λ≥200 nm a separate second peak can no longer be resolved. However, the spectrum of the NCA with Λ=200 nm (FIG. 7) is asymmetrically broadened on the high energy side, indicating the possibility of additional spectral features.

Short wavelength bands next to the plasmon of the nanostructures have been observed previously in extinction measurements of regular arrays of smooth nanodiscs on gold and were successfully ascribed to propagating surface plasmons or standing waves due to Bragg scattering at the nanoparticle array on top of the gold film. These models have, however, only limited applicability in our scattering analysis of NCAs because the investigated array geometries do not fulfill the grating coupling conditions at our illumination angle (see below) in the investigated wavelength range; in addition the correspondence between calculated Bragg scattering resonances and the measured high energy is approximate at best. Due to the experimental geometry of the performed scattering experiments an alternative explanation for the short wavelength bands arises from the possibility that the periodic two-dimensional structure of gold nanoparticle clusters on top of a transparent 10 nm thin gold film acts as a transmission grating for some components of the incident light. Diffraction of the wavelength λ incident at angle $\phi_{inc}$ on the oil immersed NCA is then described by the grating formula:

$$L(\sin \phi_{inc} + \sin \theta_{det}) = (m/n_r)\lambda \quad (1)$$

where L is cluster center-to-center separation, $\theta_{det}$ is the detection angle, m is the diffraction order, and $n_r$ is the refractive index of glass and index matching oil ($n_r$=1.5).

The incident angle $\phi_{inc}$ is determined by the numerical aperture of the darkfield condenser. For a numerical aperture of NA=1.2, $\phi_{inc}$=53°. The maximum detection angle $\theta_{det}$ is given by the marginal ray as determined by the objective numerical aperture. The numerical aperture of the objective used in these studies (NA=0.65) results in a maximum $\theta_{det}$≤25.7°. All wavelengths that fulfill equation (1) for 0°<$\theta_{det}$≤25.7° can be folded into the scattering spectrum. Following this model and considering the emission onset of the Tungsten lamp at ~400 nm we can assign peaks in the following spectral regions to diffraction at the grating: λ=400 nm-462 nm (Λ=50 nm, L=250 nm); λ=400 nm-555 nm (Λ=100 nm, L=300); λ=419 nm-647 nm (Λ=150 nm, L=350); λ=479 nm-754 nm (Λ=200 nm, L=400 nm). For larger Λ the diffracted wavelengths are shifted out of the detection range. The experimentally observed short wavelength bands all fall in the wavelength ranges predicted by equation (1). We conclude that the simple transmission diffraction grating model suffices to explain the observed dependence of the high energy band on Λ.

The frequency of the lower energy band, assigned to the cluster plasmon resonance, appears to depend weakly on the cluster edge-to-edge separation Λ as shown in FIG. 8. This effect is, however, much smaller than for the peak arising from diffraction in the investigated Λ range. The cluster resonance peak (red line) slightly blue shifts from 720 nm for Λ=50 nm separations to 690 nm for Λ=200 nm structures. At larger edge-to-edge distances the cluster plasmon resonance peak does not appear to shift further. This small blue-shift with increasing inter-particle separation is attributed to direct near-field interactions between the clusters of the arrays on the gold substrate.

Influence of Cluster Size on the Rayleigh Scattering Spectra of Nanoparticle Cluster Arrays.

As evidenced in FIG. 5, the average number of particles within the individual building blocks of NCAs can be systematically tuned by changing the diameter (D) of the binding site defined by e-beam lithography. The cluster size distribution and average cluster size n as a function of the binding size D for arrays with fixed edge-to-edge separation Λ=200 nm are quantitatively described in FIG. 9. For D=50 nm individual 40 nm gold nanoparticles are the predominant building block. However, the number of particles on the binding sites grows with D, the site diameter. The average cluster size n increases steadily from n=1.3 for D=50 nm to n=4.4 for D=120 nm and then jumps to n=19.1 for D=200 nm (see FIG. 9).

Figure 9:
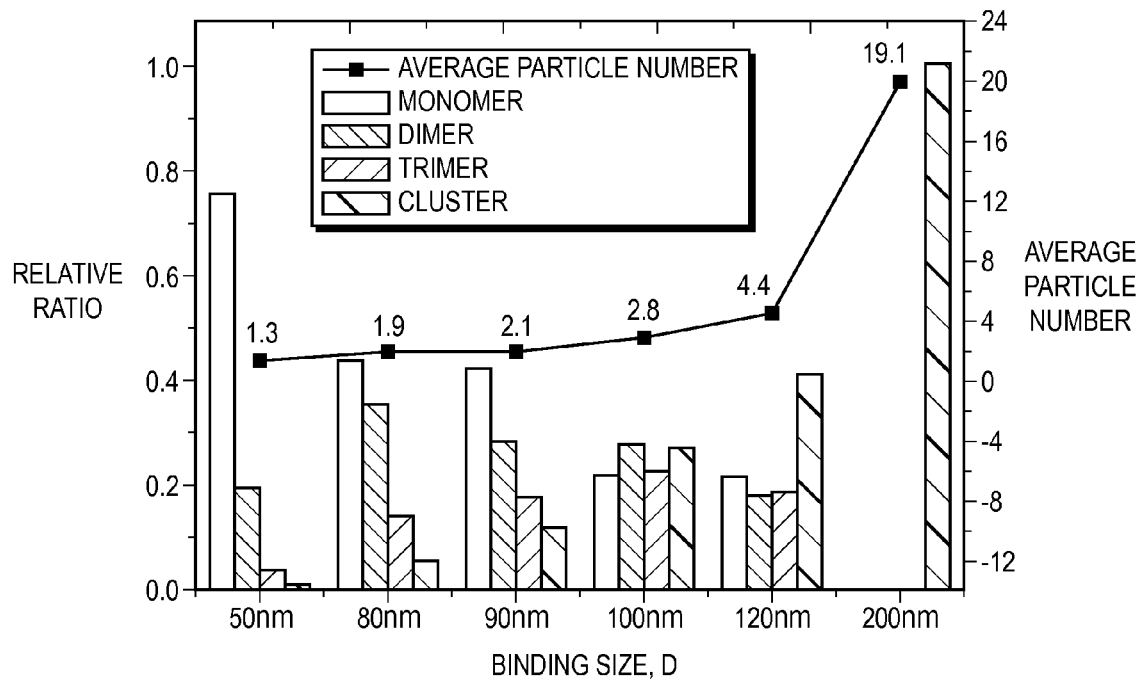
FIG. 9 is a plot of cluster size distribution as a function of size of binding site.
Figure 10:
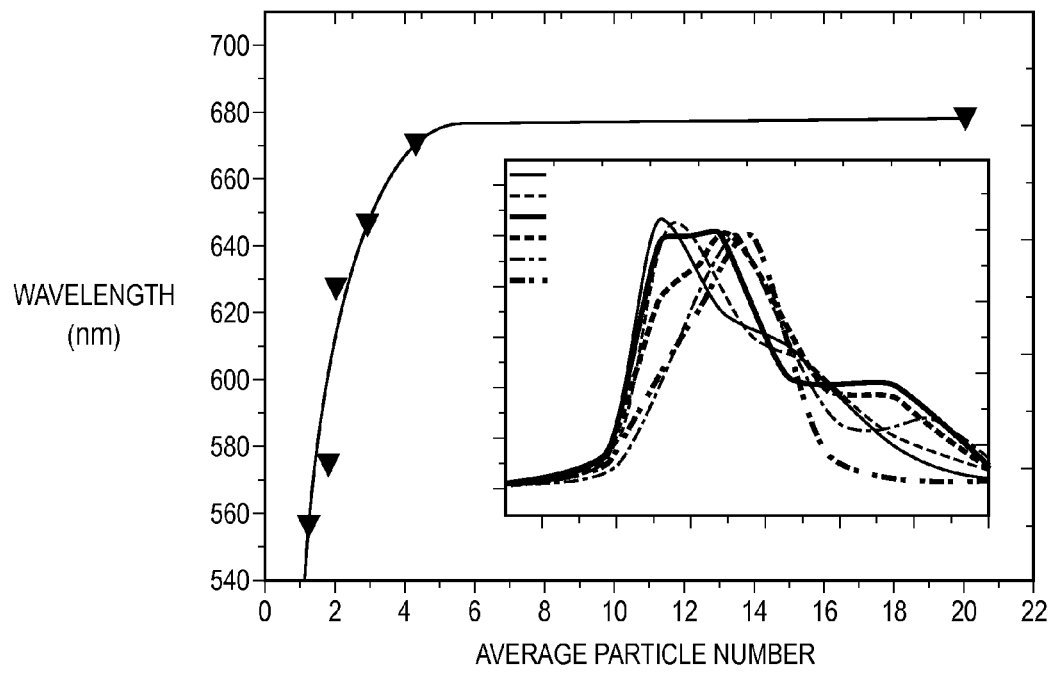
FIG. 10 is a plot of peak wavelength as a function of cluster size, along with an inset showing corresponding Rayleigh scattering spectra.

The fitted peak wavelengths of the scattering spectra recorded from the NCAs analyzed in FIG. 9 are plotted as function of n in FIG. 10. The original spectra are included as inset. The peak wavelength ($\lambda_{res}$) strongly red-shifts from 558 nm for n=1.3 to 670 nm for n=4.4. However, further increases of the cluster size beyond n=4.4 lead to only small additional redshifts of the scattering band. The peak wavelength increases only by 9 nm to $\lambda_{res}$=679 between n=4.4 and n=19.1.

The strong red-shift of the spectral response with increasing degree of particle clustering is a direct consequence of near-field coupling between the particles in the clusters, driven by the increasing number of interstitial junction plasmons as n increases. Plasmon hybridization between adjacent particle plasmons leads to coupled cluster resonances that are energetically stabilized with regard to the isolated particle plasmons. FIG. 10 shows that this stabilization saturates in larger clusters. The major portion of the energy stabilization is reached for an average cluster size of n=4.4. A further increase in the size of the clusters results in only a small additional shift of their plasmon resonance wavelength.

The red-shift due to plasmon hybridization stabilizing at around n≈4 may be understood from simple geometric considerations. A close inspection of the SEM images of the fabricated NCAs reveals that the clusters with n=4 preferentially assume a rhombohedral geometry in which the inter-particle distances are minimized (see FIG. 5 image (f)). Four gold nanoparticles at the edges of a rhombus form the unit cell of a monolayer of hexagonal closed packed spheres. This highly symmetric arrangement enables the particles to minimize the total inter-particle separation resulting in very efficient plasmon coupling. The fact that an increase in the average cluster size beyond n=4 does not lead to substantial additional spectral shifts in regular arrays therefore implies that the coupling in the larger clusters is dominated by inter-particle coupling between nearest neighbors in the unit cell.

In three-dimensional clusters additional interactions between particles along the third spatial axis (out-of-plane) can shift the plasmon resonance further into the red than observed here for two-dimensional clusters. In fact, some of the fabricated NCAs contain contaminations with larger three dimensional agglomerates due to imperfections during the fabrication process. Shoulders at wavelengths >800 nm in the scattering spectra in FIG. 10 are ascribed to these three-dimensional clusters and fractal particle assemblies. The occasional contamination of the fabricated NCAs does, however, not influence the observed global trends: the peak wavelength red-shifts in the interval 1<n<4 and converges to its maximum at n≈4.

Assembly of Regular Nanoparticle Cluster Arrays.

FIG. 11 illustrates a template guided self-assembly process to generate regular two-dimensional arrays of contiguous nanoparticles. In the first step a photoresist (PMMA) film is formed on a glass substrate covered by a thin noble metal layer (e.g., 10 nm gold film). A regular structure of wells or openings is then created in the PMMA film using e-beam lithography. The resulting PMMA mask covers all parts of the surface except for the anticipated binding sites. The binding sites are functionalized by assembly of a monolayer of amino-terminated PEGs (thiol-$(CH2)_{11}EG_7$-amine, EG=ethylene glycol) on the exposed gold surface. Under appropriate buffer conditions (pH<9) the monolayer is positively charged. Thus, negatively charged 40 nm colloidal gold nanoparticles readily bind on these positively charged binding sites in an electrostatic guided self-assembly process. The gold nanoparticles are passivated with a monolayer of carboxy terminated PEGs (thiol-$EG_7$-propionat, see FIG. 12). The charged polymers on the gold surfaces serve two purposes; they facilitate an efficient charge directed cluster assembly on the template and function as insulating dielectric between the particles and between the nanoparticles and the gold support.

SERS Performance of Nanoparticle Cluster Arrays.

Fabrication procedures that provide spatial control on the nanoscale are instrumental in developing SERS substrates according to rational design criteria. Our motivation for assembling arrays of clusters of nearly touching gold nanoparticles at defined locations is to reproducibly create hot-spots with high surface density to generate SERS substrates with high enhancement factors and improved enhancement reproducibility. The spectral characterization of the fabricated cluster arrays has already indicated the existence of both inter-particle and inter-cluster plasmon coupling in NCAs. In order to be able to utilize the interplay of electromagnetic interactions between individual nanoparticles in the clusters and between clusters, it is important to characterize the influence of the array specific geometry parameters $\Lambda$ and n on the relative Raman intensities. All SERS spectra in this study were excited at 785 nm. This wavelength has been shown to minimize autofluorescence from biological samples.

Influence of the Cluster Edge-to-Edge Separation $\Lambda$ on the SERS Signal.

Figure 21:
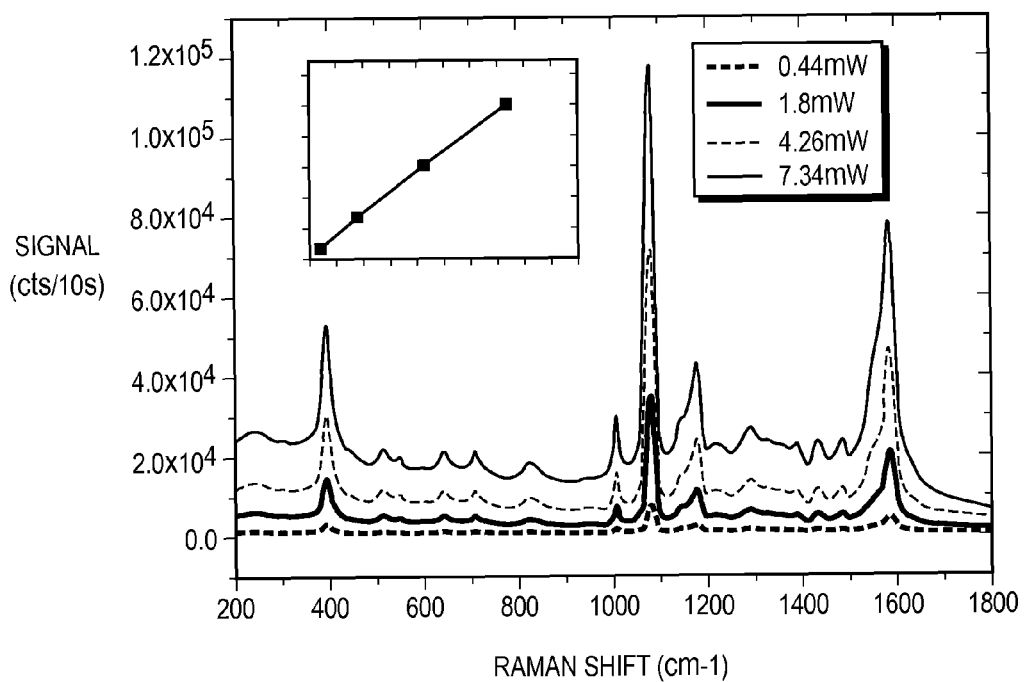
FIG. 21 is a plot of SERS spectra of a monolayer of pMA for various values of laser excitation power.
Figure 22:
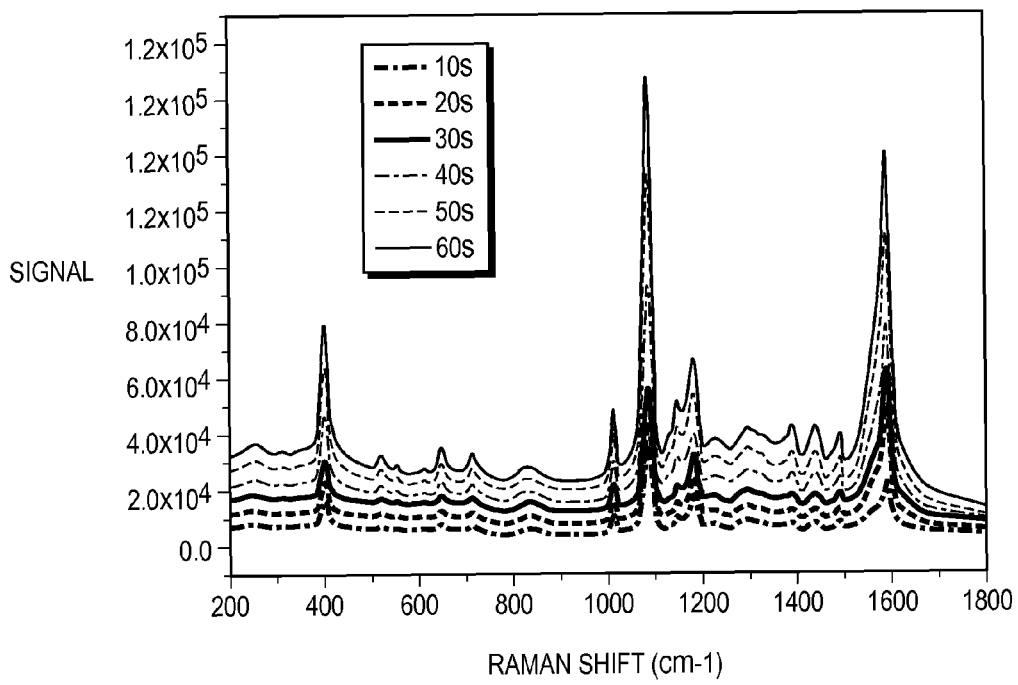
FIG. 22 is a plot of SERS signal strength as a function of integration time.

Following other SERS studies, paramercaptoaniline (pMA) was used here as a test analyte to quantify the influence of $\Lambda$ on the NCA Raman signal enhancement. To optimize the SERS performance of the substrates, the SERS signal dependence on pump power P(P=0.4 mW-7.3 mW) and data acquisition time t(t=10-60 seconds) was investigated first (see FIGS. 21 and 22). The pMA SERS intensity on a $\Lambda$=200 nm, D=200 nm NCA was found to be linearly dependent on P and t. SERS substrates with good/excellent signal to noise are obtained with 10 seconds of data collection and P=1.8 mW. All SERS measurements subsequently reported were performed with these acquisition parameters unless otherwise stated.

Figure 13:
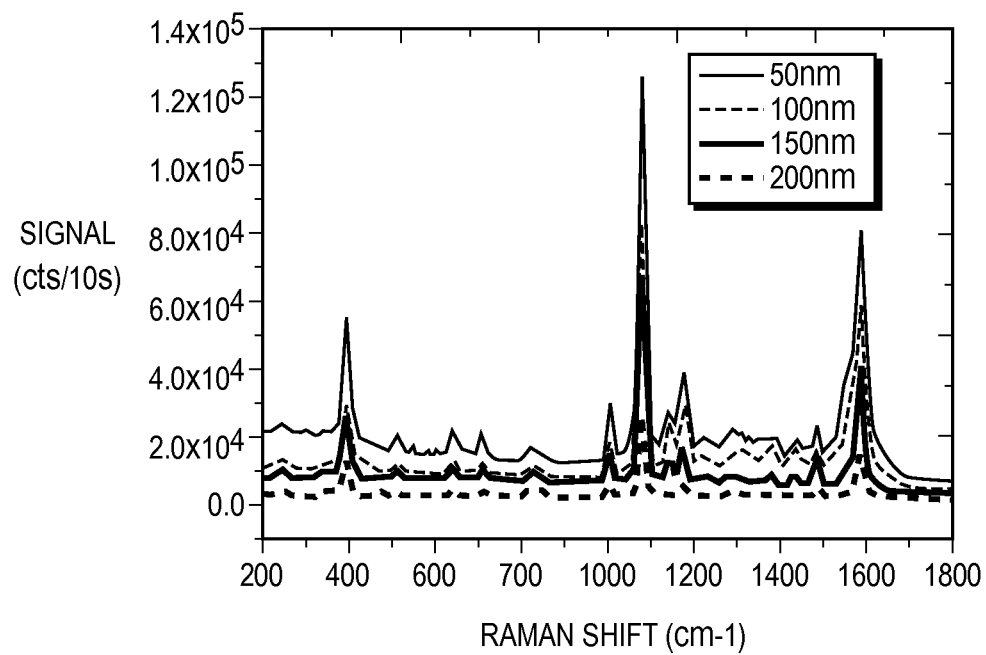
FIG. 13 is a plot of SERS spectra of a monolayer of pMA for various values of inter-cluster separation.
Figure 14:
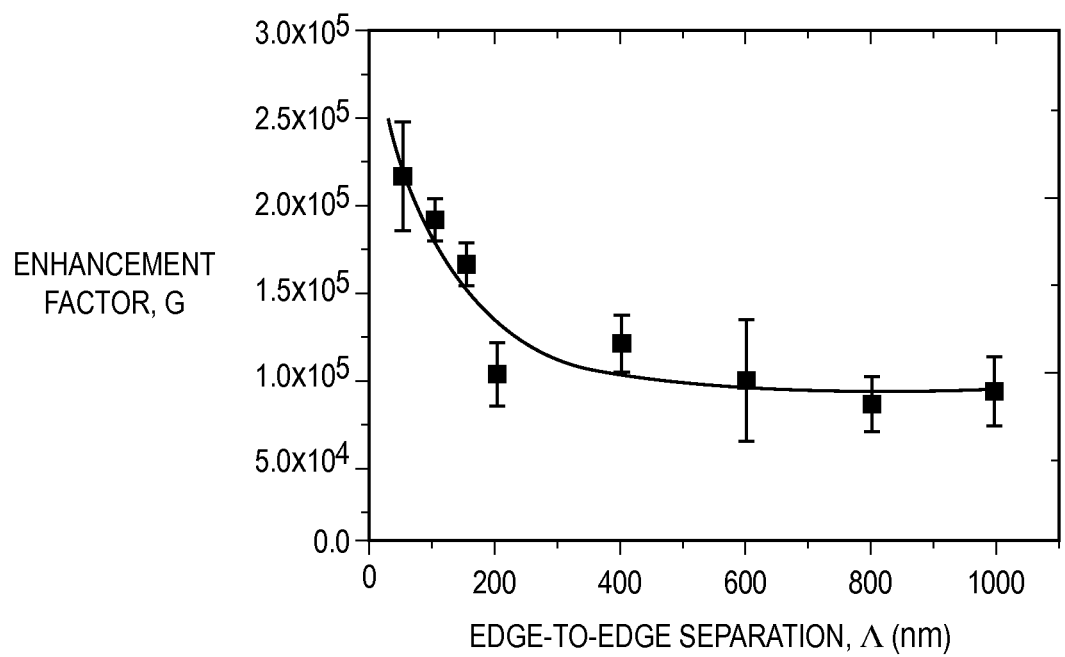
FIG. 14 is a plot of SERS enhancement factors for a monolayer of pMA as a function of inter-cluster separation.

FIG. 13 contains pMA SERS spectra from NCAs with different values of $\Lambda$ but with fixed nanoparticle binding sizes (D=200 nm). Two effects contribute to the strong increase of the SERS intensity with decreasing edge-to-edge separation. Firstly, the density of the nanoparticle clusters and therefore the total SERS active area in the scattering volume increases with decreasing $\Lambda$. Secondly, the NCA scattering spectra as function of inter-cluster separation (FIG. 8) reveals that for short edge-to-edge separations $\Lambda$<200 nm additional inter-cluster coupling further enhances the local |E|-field. Such a local field enhancement effect is evident from a comparison of SERS enhancement factors, G, as function of $\Lambda$. The absolute values of these enhancement factors are only approximates since the surface coverage with pMA, the accessible surface area of the clusters, the contribution of the gold substrate, as well as the number of molecules in the reference sample have to be estimated (see Methods section). Nevertheless, they facilitate a quantitative comparison of the relative SERS performances of samples with different filling fractions (i.e. different $\Lambda$), prepared under otherwise identical conditions. The approximate enhancement factors obtained for the 1077 $cm^{-1}$ band of pMA on NCAs with constant binding site diameter (D=200 nm) are plotted as function of $\Lambda$ in FIG. 14.

The measured SERS enhancement decreases from $2.2 \cdot 10^5$ for $\Lambda$=50 nm to $1 \cdot 10^5$ for $\Lambda$=200 nm. For even larger edge-to-edge separations the SERS enhancement is essentially independent of $\Lambda$. The gain in G at short inter-cluster separations is in agreement with the observed spectral red-shift of the plasmon resonance and is consistent with increasing near-field interactions between the clusters for $\Lambda$<200 nm. The near-field inter-cluster interactions increase the SERS enhancement generated by individual clusters by a factor of ~2 with respect to the isolated clusters at the smallest $\Lambda$ tested in this study. This observation further corroborates that plasmon coupling in NCAs occurs on two relevant length scales: inter-particle in the clusters and inter-cluster in the arrays.

Influence of Cluster Size on the SERS Signal.

Figure 15:
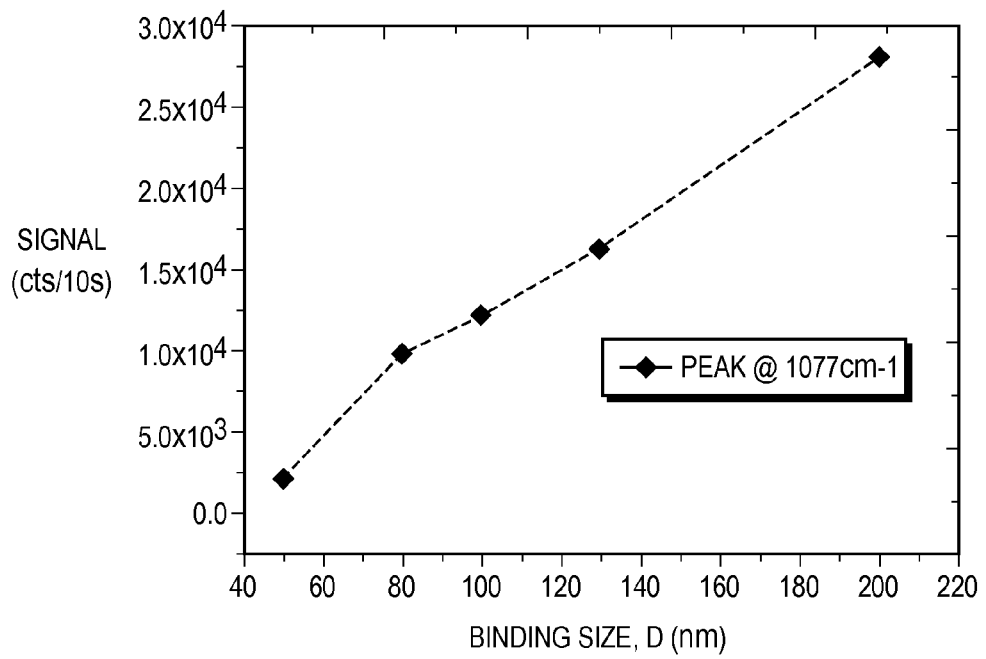
FIG. 15 is a plot of SERS intensity for a monolayer of pMA as a function of binding site size.
Figure 16:
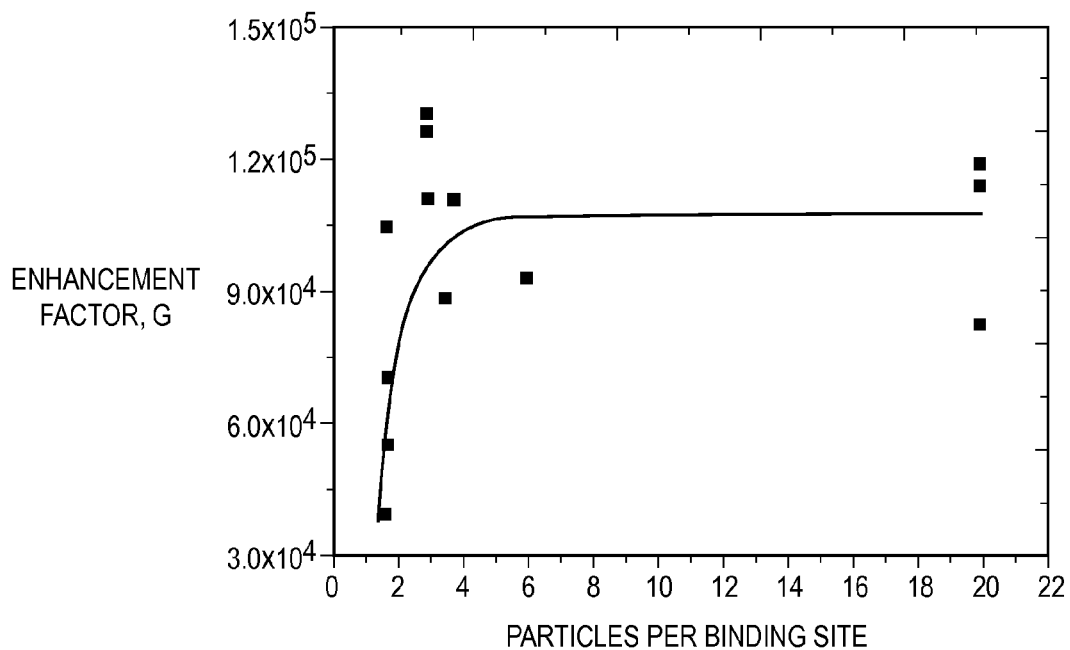
FIG. 16 is a plot of SERS enhancement factor for a monolayer of pMA as a function of cluster size.

The SERS enhancement as a function of the binding size diameter D, and thus the average cluster size, n, in NCAs with fixed edge-to-edge separation $\Lambda$ have also been investigated. In FIG. 15 the SERS intensities of the pMA 1077 $cm^{-1}$ transition of NCAs with five different D values (50 nm, 80 nm, 100 nm, 130 nm, 200 nm) and fixed edge-to-edge separation ($\Lambda$=200 nm) are compared. All of these nanoparticle cluster arrays were fabricated on the same chip to minimize intensity effects due to pMA concentration or pump power variability. The recorded signal intensity increases nearly linearly with growing D. It is a priori unclear how much a potential cluster size dependence of the SERS enhancement contributes to the signal intensity gain. The influence of D on the SERS enhancement was therefore estimated by calculating the SERS enhancement factors G as function of $\Lambda$ (see FIG. 16). The general trend in FIG. 16 indicates that G does not continuously increase with cluster size n but converges against a maximum enhancement at n≈3-4. In the case of NCAs with fixed $\Lambda$=200 nm a maximum enhancement factor of G≈$1 \cdot 10^{-5}$ is reached. This behavior corroborates the trends observed for the plasmon resonance wavelength.

The stagnation of the resonance wavelength at n≈4 in FIG. 10 is rationalized by a maximization of the inter-particle near-field interactions in compact cluster geometries. In addition, in clusters of three or four particles with triangular or rhombal cluster geometry all particles can be arranged in a "first coordination shell" around a central cavity. Analyte molecules located in this space can potentially experience very high local fields leading to strong SERS enhancements highlighting the value of the first interstitial coordination shell for SERS signal enhancement.

Benchmarking NCAs with Competing SERS Substrates Using Paramercaptoaniline (pMA) as Test Substance.

Performance of NCAs was evaluated by direct comparison with two commonly used SERS substrates: (1) non-patterned 40 nm gold nanoparticle films and (2) periodic two-dimensional arrays of gold nanodisc arrays. The non-patterned colloid films were conveniently generated on the same substrate next to the nanoparticle cluster arrays by simply removing the photoresist from a large area in the vicinity of the surface pattern during the e-beam writing step. All subsequent processing steps were identical to the procedures described above for the production of the nanocluster particle arrays. The nanodisc arrays were fabricated on a 10 nm thin gold film following standard procedures. In short, a PMMA mask was generated on top of a gold coated glass slide using direct writing e-beam lithography with subsequent development. Then a 40 nm thick gold layer was thermally evaporated onto the patterned surface and the PMMA mask was removed in a final lift-off step releasing the regular gold nanodisc pattern. The NCAs used for the benchmarking had an edge-to-edge separation of $\Lambda=200$ nm and a cluster binding size of D=200 nm. The nanofabricated nanodisc arrays had the same edge-to-edge distance and total diameter as the NCAs.

Figure 17:
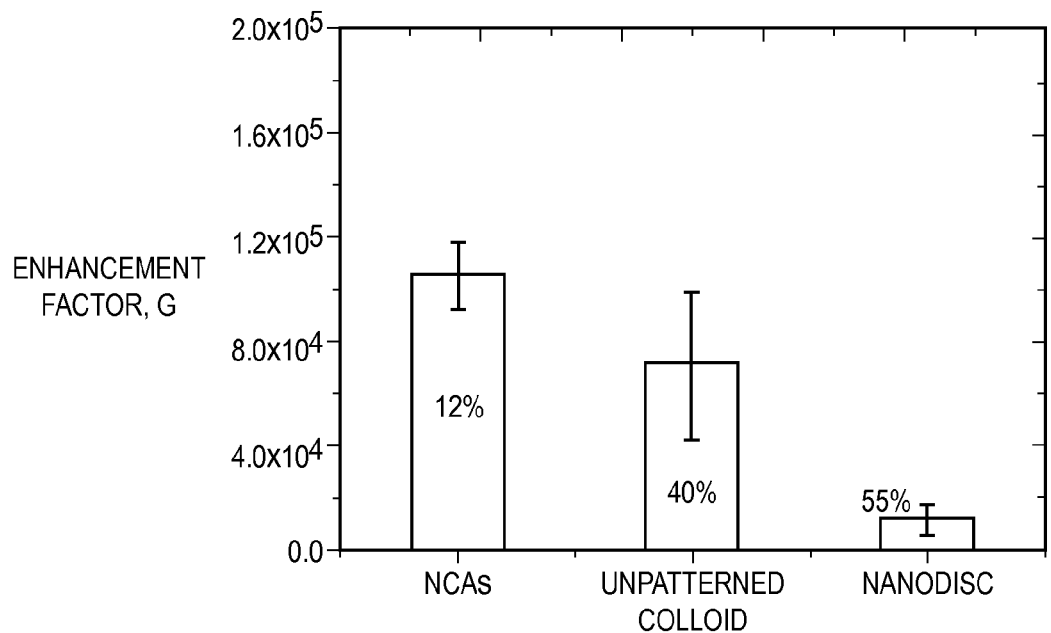
FIG. 17 is a plot showing a comparison of SERS enhancement factors for different types of SERS substrates.

The relative SERS performance of these three different substrates was evaluated in direct comparison under identical conditions. The Raman enhancement (G) factors at 785 nm for the 1077 $cm^{-1}$ mode of pMA and corresponding representative SEM images of the investigated substrates are summarized in FIG. 17. These values correspond to twelve measurements from three different substrates for each substrate type. The NCA substrates yielded the overall largest G values ($\sim 1.1 \cdot 10^5$), followed by the non-patterned nanoparticle film ($\sim 7.0 \cdot 10^4$). The nanodisc array exhibited the smallest G values ($\cdot 1.0 \cdot 10^4$). NCAs with $\Lambda=50$ nm, D=200 nm yielded the maximal enhancement factor of $G=2.2 \cdot 10^5$ for the substrates prepared for this study (see FIG. 14). These values fall within the typical SERS enhancement range of gold island films and are comparable with those obtained with other engineered SERS substrates such as gold nanohole arrays. Although enhancement factors up to $1 \cdot 10^8$ have been observed in some cases for e-beam patterned gold nanodisc arrays fabricated on a gold film, the NCAs are found to provide a significantly higher ($\sim 1$ order of magnitude) Raman signal enhancement than the corresponding nanodisc arrays at least for pMA excited at 785 nm.

The observation that the NCAs provide a stronger SERS signal enhancement than smooth nanodisc arrays is readily ascribed to the fact that the NCAs have a much higher degree of roughness than the nanodiscs due to crevices, holes, and junctions between the nanoparticles in the clusters. The incident field can be effectively localized in these nano-roughened structures leading to overall higher enhancement factors. Nanoscale roughness cannot, however, account for the fact that the ensemble averaged SERS enhancement factors for NCAs are also slightly higher than those of the non-patterned gold nanoparticle films which also contain nanoparticle clusters. Based on the observed dependencies of the ensemble averaged G factors on $\Lambda$ and n, we propose the following model to account for the observed differences between patterned and non-patterned colloid substrates: the SERS enhancement factors of individual two dimensional nanoparticle clusters saturates at around $n \approx 4$. In an array of patterned clusters the total SERS enhancement of the individual clusters can be further increased through cumulative electrodynamic interactions occurring on two different length scales. On the length scale of a few tens of nanometers (intercluster length scale) the cluster plasmons couple and provide a first stage of strong enhancement of the incident electric field. This enhanced field is then further increased by the intra-cluster coupling between the individual particles of the clusters. The phenomenon therefore consists of a sequential enhancement similar to the effects observed in RF Yagi antennas or optical nanolenses.

Figure 18:
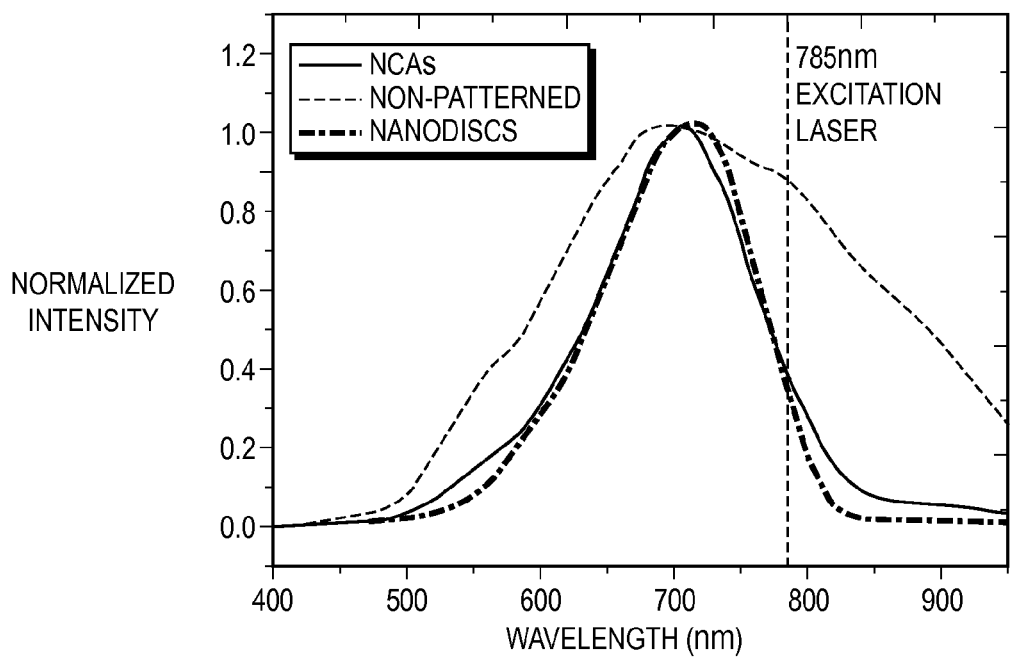
FIG. 18 is a plot showing Rayleigh scattering spectra for the different types of SERS substrates of FIG. 17.

As discussed elsewhere, the Raman signal enhancement can be maximized by matching the excitation wavelength with the absorption band of the plasmonic SERS substrate. FIG. 18 shows the normalized spectra of the investigated NCAs, smooth gold nanodisc arrays, and non-patterned colloid films. Whereas NCAs and nanodisc arrays show well defined plasmon resonances at around ~700 nm with a full width at half maximum (FWHM) extending from 630 nm to 780 nm, the non-patterned colloid film shows a much broader scattering spectrum with FWHM between 580 nm and 880 nm. We ascribe this spectral broadening to a wide distribution of cluster sizes including three-dimensional and fractal aggregates in the non-patterned colloid film.

The measured relative Rayleigh scattering intensities for NCAs and nanodisc arrays have decreased to ~30% of their peak intensity value at the SERS excitation wavelength of 785 nm. In contrast, for the non-patterned colloid substrate the scattering cross-section is close to its peak value at the 785 nm SERS excitation wavelength. The detuning between 785 nm Raman excitation wavelength and the resonance scattering maxima evident in FIG. 18 suggests that—unlike the non-patterned colloid films—the enhancement factors of NCAs can be significantly increased by improving the match between resonance wavelength and excitation laser wavelength. This can be achieved either by using a laser with an emission wavelength around 700 nm or by shifting the resonance wavelength of the arrays closer to 785 nm by exchanging spherical 40 nm gold nanoparticles with building blocks that have energetically lower particle resonances.

Another important SERS performance characteristic, in addition to the signal enhancement, is the reproducibility of the enhancement factors generated by different SERS substrates. The reproducibility of the enhancement factor (G) is captured here by the coefficient of variability, i.e. the standard deviation of G values given by twelve independent measurements on four different substrates, expressed as a percentage of the mean G value for each substrate type. These variability coefficients are given in FIG. 17. As evident from this measure for G reproducibility, the variations of the NCAs enhancement (12%) is much smaller than that observed on either the non-patterned colloid substrate (41%), or the nanodiscs (56%). Thus both in terms of absolute enhancement and repeatability, the NCAs outperform the other two substrate types tested here.

SERS Bacterial Detection and Identification Using NCAs.

The SERS performance of NCAs makes them potentially useful candidates for complex sensing applications such as whole cell fingerprinting. There is currently significant interest in developing SERS for the rapid characterization and identification of bacterial pathogens. Due to the distance dependence of the field enhancement, SERS selectively probes the molecular components of the outer layer of bacterial cells where chemical distinctions appear to be the greatest thus enhancing specificity and may therefore be a promising tool for bacterial diagnostics. The successful application of SERS for this analytical application requires substrates that can provide strong and reproducible enhancements for these organisms at the single cell level and have a storable shelf life in the 6-12 month range.

In the case of bacteria the surface morphology and the binding affinity to the substrate are extremely important and can influence both the detected vibrational bands and the total signal intensities. Not all SERS active substrates provide SERS spectra of whole bacterial cells. Only if a bacterial cell can effectively attach to the surface such that characteristic surface moieties are near SERS active sites will a strong Raman signal be observed.

Figure 19:
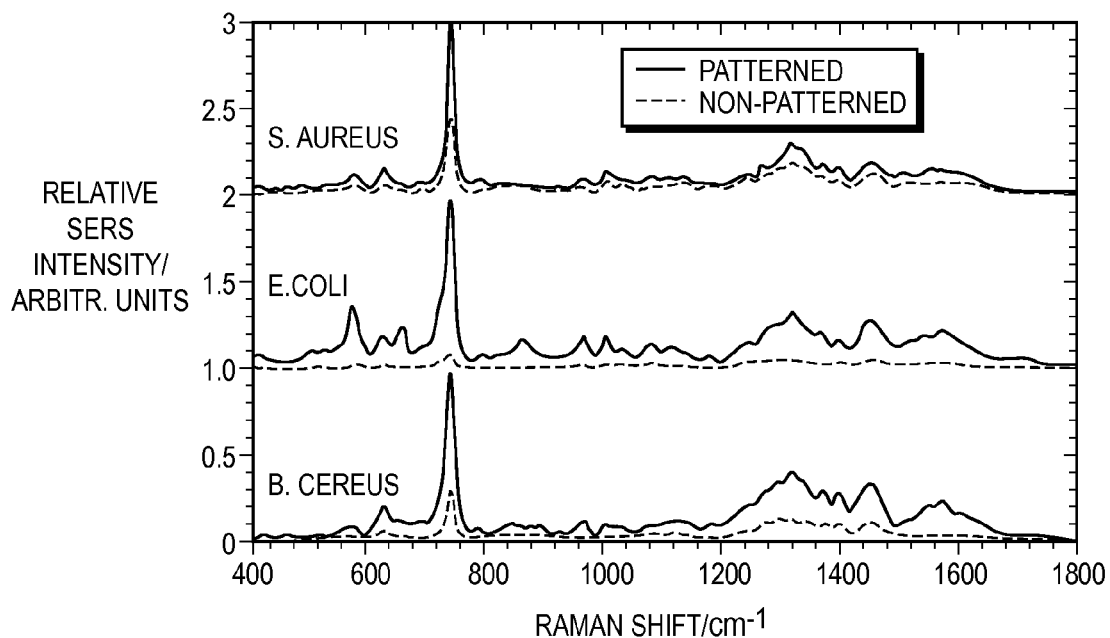
FIG. 19 is a plot showing SERS spectra of three different bacteria *S. aureus*, *E. coli*, and *B. cereus*.

In order to test the ability of the NCAs, the non-patterned colloid films, and the nanodiscs to act as effective substrates for the observation of SERS spectra of vegetative bacterial cells, suspensions of three different bacterial species (*Staphylococcus aureus, Escherichia coli*, and *Bacillus cereus*) were placed on these substrates and SERS spectra excited at 785 nm (4.3 mW power, 10 seconds integration time) were acquired. Only very weak bacterial SERS spectra could be observed on the nanodisc arrays. However, both patterned (NCA) and non-patterned colloid substrates provided quantifiable SERS signals. FIG. 19 shows representative SERS spectra (single scan) of *S. aureus*, *E. coli*, and *B. cereus* obtained from NCA and smooth (40 nm height) nanodisc arrays, both with 200 nm diameter and 200 nm edge-to-edge separation features. The non-patterned gold nanoparticle substrates were located on the same chip in close vicinity to the nanoparticle cluster array to ensure that these two samples were always measured under identical experimental conditions. As seen in FIG. 19, SERS spectra of bacteria are stronger on the NCA substrates than on the non-patterned colloid films. Furthermore, in contrast to the NCA bacterial spectra, the bacterial SERS signal intensities exhibited strong variations at different positions on the non-patterned substrates.

The bacterial SERS spectra share many common spectral features as evident in FIG. 19 and has been discussed previously. Identification of the chemical species responsible for the vibrational bands in the SERS spectra of bacteria has not yet been achieved and is beyond the scope of this current report. However, the unique SERS vibrational signatures provide the basis for a rapid bacterial identification methodology when combined with multivariate library searching techniques.

Figure 20:
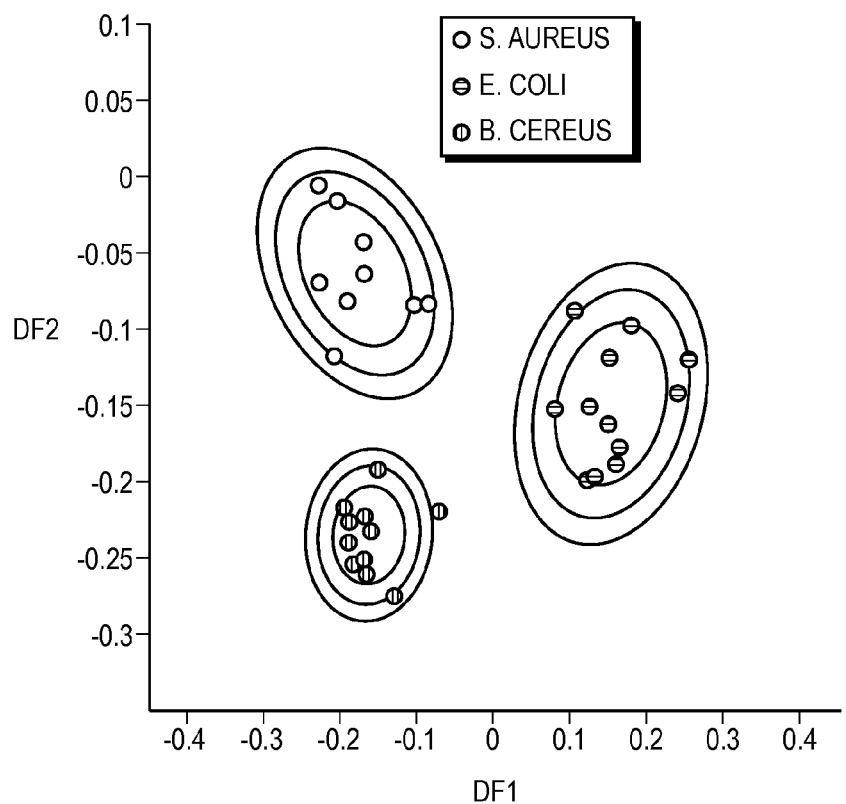
FIG. 20 is a discriminant function analysis (DFA) plot derived from the data of FIG. 19.

The ability of NCAs to be used for bacterial diagnostics is demonstrated in FIG. 20. It has been shown previously how a principal component analysis (PCA) based on the sign of the second derivative of the SERS spectra provides improved specificity for the identification of bacterial species and strains. The SERS spectra are thus reduced to a series of zeroes and ones, i.e. barcodes, as input for unsupervised clustering algorithms such as PCA, or consequent supervised methods such as discriminant function analysis, hierarchical cluster analysis, or neural network techniques. Here the specificity of these SERS based signatures on NCAs is shown by the results of a discriminant function analysis (DFA) based on the barcode reduced SERS spectra of *S. aureus*, *E. coli*, and *B. cereus*. The discriminant functions are linear combinations of the first four PCs which capture 98% of the variance of this 30 spectra data set.

As seen in the DF2 vs. DF1 plot in FIG. 20, the SERS signature of *B. cereus*, *E. coli*, and *S. aureus* obtained on the NCAs are well separated forming non-overlapped regions. The rings in each of the cluster regions correspond to tow dimensional standard deviations centered on the mean for each species cluster. The large standard deviation separations between these clusters of the tested clusters of the tested bacteria indicate that the NCAs enable a spectral signature capable of bacterial identification. Work is currently ongoing to determine the best performing SERS substrates for this purpose based on the criteria of Raman enhancement strength, spectral reproducibility, substrate storage lifetime and commercial scalability.

It is shown that nanoparticle cluster arrays (NCAs) provide reproducible SERS signals from different bacteria species including *Bacillus cereus, Escherichia coli*, and *Staphylococcus aureus*. The NCAs enabled a spectroscopic discrimination of these samples through SERS in combination with multivariate data analysis techniques. The NCAs used for this analytical challenge were fabricated by combining top down nanofabrication and bottom-up self assembly procedures in a template guided self-assembly process. This approach provides control over the size of the particle clusters and their spatial location on the nanoscale. We used this process to fabricate regular arrays of 40 nm gold nanoparticle clusters of defined cluster size n and cluster edge-to-edge separation $\Lambda$ over several hundred square microns. The photonic-plasmonic scattering resonances of the arrays as function of n and $\Lambda$ were characterized. The spectra are dominated by the ensemble resonance of the gold film supported nanoparticle clusters at large cluster separations. For NCAs with short inter-cluster separations, $\Lambda < 200$ nm, we also observe an additional short wavelength band which we ascribe to light diffraction from the NCAs acting as transmission grating for the incident light. A systematic variation of $\Lambda$ revealed that the plasmon resonance peak red-shifts with decreasing $\Lambda$ for edge-to-edge separations $\Lambda < 200$ nm indicating additional inter-cluster near-field interactions. The red-shift of the plasmon resonance is accompanied by an increase in the SERS enhancement for $\Lambda \leq 200$ nm. This observation confirms that electrodynamic interactions between the clusters can further increase the Raman signal intensity generated by individual isolated clusters, and we conclude that the net enhancement is the result of a multiscale field enhancement in NCAs. Next to the edge-to-edge separation, the SERS signal enhancement also depends on the cluster size n, and we investigated the optical response and the SERS enhancement of NCAs as function of n. The cluster resonances of the arrays strongly red-shift with increasing cluster size n up to $n \approx 4$. We did not observe a further significant increase in the enhancement for larger two-dimensional nanoparticle clusters. Similarly, the Raman signal enhancement shows a significant increase with growing cluster size for small cluster sizes $n \approx 4$ but remains essentially constant for larger cluster sizes. This behavior suggests that for n=4 cluster structures are accessible which enable very efficient plasmon coupling between all particles of the clusters. We find that one of the preferred structures for n=4 is the rhombus which is the unit cell of a two-dimensional close packing. The size dependency of the SERS enhancement indicates a dominance of the interstitial first shell in the Raman signal amplification.

Overall, it is revealed that NCAs can be used to engineer SERS substrates whose spectral and field localization properties can be controlled systematically by varying n and $\Lambda$. We benchmarked NCAs with non-patterned two-dimensional gold nanoparticle substrates and regular gold nanodisc arrays. We found that NCAs offer a good compromise between signal enhancement and substrate reproducibility. In addition, the NCAs clearly outperformed the other substrates in SERS measurements of bacteria. Future steps for further improvement and optimization of the SERS enhancement by NCAs will involve the study of the nanoparticle composition, size, and shape as well as the geometric patterns of the arrays.

While various embodiments of the invention have been particularly shown and described, it will be understood by those skilled in the art that various changes in form and details may be made therein without departing from the spirit and scope of the invention as defined by the appended claims.

What is claimed is:

1. A method of making a substrate for use in surface-enhanced Raman spectroscopy, comprising:
    forming a planar substrate layer; and
    using a template-guided chemical self-assembly process to create a nanoparticle cluster array of defined size with nanoscale inter-particle separations at predefined pattern locations on the planar substrate layer, the template-guided chemical self-assembly process including:
        forming a template on the planar substrate layer, the template defining an array of binding sites for respective nanoparticle clusters of the nanoparticle cluster array, the template further defining a deterministic binding site width D and a cluster separation $\Lambda$, $\Lambda$ being a deterministic distance between adjacent nanoparticle clusters;

depositing nanoparticles with selective binding at the binding sites through the template, a nominal number n of tightly-packed nanoparticles being deposited at each binding site based on a nominal size of the nanoparticles and the deterministic binding site width D; and subsequently removing the template from the planar substrate layer, and further including the steps, performed prior to depositing the nanoparticles, of:

functionalizing the substrate layer with a first monolayer that becomes positively charged under buffer conditions existing when the nanoparticles are deposited; and passivating the nanoparticles with a second monolayer that readily binds to the positively charged first monolayer at the binding sites when the nanoparticles are deposited.

2. A method according to claim 1, wherein depositing the nanoparticles includes placing a nanoparticle-containing colloidal solution on the binding sites, incubating to effect binding of the nanoparticles to the binding sites, and then washing to remove non-bound nanoparticles.

3. A method according to claim 1, wherein forming the template includes e-beam lithographic patterning of a deposited layer of photoresist.

4. A method according to claim 1, wherein n is determined by the radius of the nanoparticles and morphology and width D of the binding.

5. A method according to claim 4, wherein the nanoparticles are made of a material selected from silver, copper, silver-gold alloys, and aluminum.

6. A method according to claim 4, wherein the nanoparticles shapes are selected from non-spherical and/or hollow, core-shell nanoparticles and multi-scale aggregates of different size/shape nanoparticles.

7. A method according to claim 4, wherein the nanoparticles are mixed dielectric and metallic structures.

8. A method according to claim 1, wherein the nanoparticles are dielectrically coated gold nanoparticles and the planar substrate layer includes a gold film.

9. A method according to claim 1, wherein the first monolayer includes amino terminated polyethylene glycol.

10. A method according to claim 1, wherein the second monolayer includes carboxy terminated polyethylene glycol.

* * * * *